US007892522B2

(12) United States Patent
Johnson et al.

(10) Patent No.: US 7,892,522 B2
(45) Date of Patent: *Feb. 22, 2011

(54) CONTRAST AGENTS

(75) Inventors: David Johnson, Wayne, PA (US); Jonny Østensen, Oslo (NO); Morten Eriksen, Oslo (NO); Audun Tornes, Oslo (NO); Sigmund Frigstad, Oslo (NO); Harald Dugstad, Oslo (NO); Jo Klaveness, Oslo (NO); Pål Rongved, Oslo (NO); Roald Skurtveit, Oslo (NO); Jorunn Brænden, Oslo (NO)

(73) Assignee: GE Healthcare AS, Oslo (NO)

( * ) Notice: Subject to any disclaimer, the term of this patent is extended or adjusted under 35 U.S.C. 154(b) by 355 days.

This patent is subject to a terminal disclaimer.

(21) Appl. No.: 09/950,985

(22) Filed: Sep. 13, 2001

(65) Prior Publication Data

US 2002/0106328 A1 Aug. 8, 2002

Related U.S. Application Data

(63) Continuation of application No. 09/241,419, filed on Feb. 2, 1999, now abandoned, which is a continuation of application No. PCT/GB97/02119, filed on Aug. 4, 1997.

(30) Foreign Application Priority Data

Aug. 2, 1996 (GB) ................................. 9616301.9
Mar. 21, 1997 (GB) ................................. 9705918.2

(51) Int. Cl.
*A61B 8/00* (2006.01)
*A61K 9/127* (2006.01)
*A61B 8/14* (2006.01)

(52) U.S. Cl. .................. 424/9.52; 424/450; 600/458
(58) Field of Classification Search ............. 424/9.5, 424/9.51, 450, 9.52; 600/458
See application file for complete search history.

(56) References Cited

U.S. PATENT DOCUMENTS 5,540,909 A * 7/1996 Schutt ........................ 424/9.52
5,599,523 A * 2/1997 Beller et al. ................. 424/9.52
5,773,024 A * 6/1998 Unger et al. ................. 424/450
6,054,118 A * 4/2000 Østensen ..................... 424/9.52

FOREIGN PATENT DOCUMENTS

| GB | 2 129 685 A | 5/1984 |
| WO | WO 96 08234 A | 3/1996 |
| WO | WO 97 29782 A | 8/1997 |
| WO | WO 97 29783 A | 8/1997 |

OTHER PUBLICATIONS

Maruyama, Kazuo, et al. "Lipid composition is important for highly efficient target binding and retention of immunoliposomes", Proc. Natl. Acad. Sci. U.S.A., 1990, XP002060195.
Liu, Dexi, et al. "Recognition and clearance of liposomes containing phosphatidylserine are mediated by serum opsonin", Biochim. Biophys. Acta, 1995, XP002061182.
Liu, D., et al. "Role of Liposome Size and Res Blockade in Controlling Biodistribution and Tumor Uptake of GM1 Containing Liposomes", Biochim. Biophys. Acta., 1992, XP002061183.
Scherphof, G. L., et al. "Cells involved in removing liposomes from the blood circulation: Why are they so special?", Journal of Liposome Research, 1996, XP002061184.
Unger, E., et al. "Gas Filled Lipid Bilayers as Imaging Contrast Agents", Journal of Liposome Research, Jan. 1, 1994, XP000537462.
Porter, T. K., et al. "Effect of microbubble gas molecular weight on myocardial contrast produced from an intravenous injection", 68th Scientific Session of the American Heart Association, Anaheim, California, USA, Nov. 13-16, 1995, XP002060196.
Bigon, E., et al. "Pharmacological Effects of Phosphatidylserine Liposomes: The Role of Lsyophosphatidylserine", British Journal of Clinical Pharmacology, Sep. 1, 1979, XP000603415.
Farge, E., "Increased vesicle endocytosis due to an increase in the plasma membrane phosphatidylserine concentration", Biophysical Journal, Dec. 1995, XP002061185.

* cited by examiner

*Primary Examiner*—Yong S Chong (57) ABSTRACT

Ultrasound contrast agents comprising microbubbles of biocompatible gas, e.g. a sulphur halide or a perfluorocarbon, stabilized by opsonisable amphiphilic material, e.g. a membrane-forming lipid such as a phospholipid, especially a negatively charged phospholipid such as a phosphatidylserine, may exhibit prolonged contrast-generating residence time in the liver following intravenous administration.

10 Claims, 4 Drawing Sheets

CONTRAST AGENTS

This application is a continuation of U.S. patent application Ser. No. 09/241,419 having a filing date of Feb. 2, 1999 now abandoned (of which the entire disclosure of the pending, prior application is hereby incorporated by reference), which is itself a continuation of international patent application number PCT/GB97/02119 having a filing date of Aug. 4, 1997.

This invention relates to ultrasound imaging, more particularly to methods of ultrasound imaging of the liver and to contrast agents useful in such methods by virtue of their prolonged residence time in the liver.

Cancers such as hepatomas and metastatic spreads to the liver are major causes of death in the industrialised world and there is a continuing need for improved methods of tumour detection. Investigations of the liver may, for example, be performed by X-ray imaging, e.g. following administration by injection of a liposome-encapsulated iodinated X-ray contrast agent. Thus, as described in WO-A-8809165, such liposomes become fixed in the liver and spleen through interaction with the reticuloendothelial system, permitting X-ray examination of these organs; in general tumour tissue has different vascularity from and/or fewer absorption sites than healthy tissue and so may be detected as an area of modified contrast.

As noted in WO-A-8809165, X-ray examination of the liver typically requires the iodinated X-ray contrast agent to be present therein at a concentration of 2-2.5 mg iodine/g tissue, i.e. in a total amount of ca. 3.5 g in the case of a human adult liver weighing ca. 1.5 kg. It is suggested that a 40% uptake of liposomes by the liver is typical, so that injection of contrast agent containing ca. 9 g iodine will be required to produce this level. This may involve concomitant injection of up to 9 g lipid, which could lead to undesirable side effects.

Ultrasound examination of the liver is potentially of great interest by virtue of the substantially reduced cost of ultrasound scanners compared to X-ray and computed tomography (CT) scanners, the avoidance of use of ionising radiation (potentially enhancing safety for both patients and medical staff), and the reduced doses of contrast agents which may be required. Thus, in this last regard, it is well known that contrast agents comprising dispersions of microbubbles of gases and/or volatile fluids are particularly efficient backscatterers of ultrasound by virtue of the low density and ease of compressibility of the microbubbles; such microbubble dispersions, if suitably stabilised, may permit highly effective ultrasound visualisation of, for example, the vascular system and tissue microvasculature, often at advantageously low doses. However, while such contrast agents are typically removed from the vasculature through uptake by the reticuloendothelial system, e.g. in the liver, spleen or lymphatic nodes, existing methods for imaging these organs are limited in their applications.

U.S. Pat. No. 5,425,366 discloses that whilst various types of microparticulate ultrasound contrast agents, e.g. gas-containing polymer microcapsules, are taken up by the liver they do not permit effective imaging using conventional B-mode techniques. It is suggested that this is because the irradiated ultrasound signal has only a small penetration depth into the liver tissue as a result of cumulative reflection by the contrast agent, leading to uniform shadowing. It is equally likely, however, to be the result of attenuation of the irradiated ultrasound signal through interaction with the structural material of the microparticles, e.g. leading to absorption of the signal and conversion to heat.

It is suggested in U.S. Pat. No. 5,425,366 that, although such microparticulate contrast agents retained in organs such as the liver are essentially motionless, they may nonetheless be visualised by colour Doppler techniques. It is proposed that the higher irradiation energy levels associated with colour Doppler investigations cause the microparticles to burst, thereby generating Doppler-sensitive signals described as "acoustically stimulated acoustic emission", although it seems likely that in practice the detector interprets the disappearance of a microparticle as a high velocity movement and generates an appropriate display. It is also noted that progressive destruction of the microparticles by the irradiated ultrasound signal will facilitate penetration of the signal deeper into the tissue as the investigation proceeds.

A disadvantage of this technique is the high attenuation exhibited by polymer-encapsulated contrast agents such as are described in the patent. This may result from the comparative rigidity of the encapsulating material and prevents generation of homogeneous signal levels throughout the liver. Scan times are therefore necessarily long and the information obtained may be difficult to interpret. The technique is therefore not suitable for ultrasound tomography. Also disadvantageous is the loss of information and image quality which inevitably results from using colour Doppler instrumentation to detect what are effectively anomalous results from essentially motionless particles. Thus the colour display of such an instrument is intended to map velocities rather than signal intensities, so that information regarding intensity may simply be lost or may be distorted, e.g. by the use of high pass filters to exclude signals arising from slowly moving tissue.

Furthermore, because of the above-noted high attenuation of microparticulate ultrasound contrast agents such as the polymer-encapsulated microcapsules described in U.S. Pat. No. 5,425,366, the backscatter:attenuation ratio is necessarily relatively low. This inevitably limits the efficiency of ultrasound imaging of other parts of the body, e.g. the vasculature, which it might be desired to study in conjunction with imaging of the liver.

There is accordingly a need for methods of ultrasound imaging using contrast agents which permit effective visualisation of the liver by means of a variety of imaging techniques, for example including conventional B-mode and harmonic imaging.

The present invention is based on the finding that contrast agents comprising microbubbles of gases stabilised by opsonisable amphiphilic materials may exhibit prolonged contrast-generating residence time in the liver and spleen. Whilst it might be expected that such amphiphilic material-stabilised microbubbles would be phagocytosed by liver and spleen macrophages, and whilst in practice the amphiphilic materials may be chosen as described in further detail hereinafter to facilitate their rapid uptake in the liver, e.g. by the Kupffer cells of the reticuloendothelial system, it is extremely surprising that their contrast-generating effect may continue, e.g. for several hours, since one would expect rapid destruction of the contrast agents and loss of echogenicity following such phagocytosis.

Thus according to one aspect of the present invention there is provided a method of ultrasound imaging which comprises administering to a human or non-human animal subject a contrast-enhancing amount of a contrast agent comprising microbubbles of biocompatible gas stabilised by opsonisable amphiphilic material, allowing at least a proportion of said microbubbles to be taken up in the liver of the subject and generating an ultrasound image of at least a part of the liver.

The invention further embraces the above-defined contrast agents for use in ultrasound imaging of the liver, as well as the use of microbubbles of biocompatible gas stabilised by opsonisable amphiphilic material in the manufacture of imaging agents for use in ultrasound imaging of the liver in human and non-human animal subjects.

The opsonisable amphiphilic material, which may if desired be fluorinated, may for example be selected from opsonisable amphiphilic lipids, opsonisable amphiphilic proteins and opsonisable amphiphilic natural and synthetic polymers.

Opsonisable amphiphilic lipid material may, for example, comprise one or more membrane-forming lipids, which term is used herein to denote amphiphilic lipids capable of forming liquid crystalline or gel state bilayers in aqueous media; such amphiphilic lipids also form monolayers or single bilayers at gas-water interfaces, e.g. as in Langmuir-Blodget films. The term thus includes lipids such as are found in biological membranes which are characterised by low water solubility such that they form liquid crystalline or gel state bilayers in aqueous media even at very low concentrations and by a tendency in aqueous solutions substantially to decrease surface tension, e.g. to almost zero. Such lipids will form encapsulating monolayers, bilayers or multiples thereof about the gas microbubbles in contrast agents used in accordance with the invention.

Examples of such membrane-forming lipids include lipopeptides, lipophilically derivatised carbohydrates, e.g. carrying one or more fatty acyl groups, mono- and di-glyceride esters of fatty acids, sphingolipids, glycolipids, glycerolipids and, more preferably, phospholipids, for example phosphatidic acids, phosphatidylcholines, phosphatidylserines, phosphatidylglycerols, phosphatidylethanolamines, phosphatidylinositols, cardiolipins and corresponding lyso (i.e. monoacyl, preferably 1-acylated) analogues thereof.

The opsonisable amphiphilic material of contrast agents used in accordance with the invention may, for example, comprise one or more such membrane-forming lipids, optionally together with additives which modify membrane properties such as stability, dispersibility, aggregation tendency, biological activity, flexibility or polarity. Representative additives include non-membrane-forming lipids, for example sterols such as cholesterol.

Advantageously at least a part, for example at least 5%, e.g at least 20%, preferably at least 50%, of any membrane-forming lipid material consists of molecules which individually bear a net overall negative charge under conditions of preparation and/or use. Thus it appears that electronic repulsion between charged lipid membranes encourages formation of stable and stabilising lipid monolayers about the gas microbubbles; the flexibility and deformability of such thin membranes significantly enhances the echogenicity of the contrast agents relative to systems wherein the gas is encapsulated by one or more lipid bilayers. Moreover, such monolayer systems exhibit substantially reduced attenuation compared to bilayer systems and so permit greater penetration of the irradiated ultrasound signal, consequently facilitating imaging at greater depth within the liver.

The presence of negatively charged membrane-forming lipid material also encourages recognition of the contrast agents by the Kupffer cells, thereby enhancing hepatic uptake, as may be confirmed by electron microscopy of the livers of e.g. rats following intravenous injection of contrast agents comprising such lipid material.

Examples of negatively charged membrane-forming lipids include negatively charged phospholipids such as naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and cardiolipins; the fatty acyl groups of such phospholipids will typically each contain about 14-22 carbon atoms, for example as in palmitoyl and stearoyl groups.

The use of contrast agents comprising phosphatidylserines is particularly preferred since the Kupffer cells and splenic macrophages recognise aged red blood cells and platelets by the presence of high concentrations of phosphatidylserine on their surfaces. They will accordingly likewise recognise and will phagocytose such phosphatidylserine-containing contrast agents in the liver and spleen.

The membrane-forming lipid or other opsonisable amphiphilic material may advantageously be selected to be substantially impermeable to the gas content of the contrast agent, at least during transport of the contrast agent by the bloodstream to the liver. This may, for example, be achieved by employing gases which exhibit relatively low rates of diffusion through lipid and like membranes. Examples of such gases include sulphur halides such as sulphur hexafluoride or disulphur decafluoride; fluorocarbons such as perfluorocarbons; fluorinated (e.g. perfluorinated) ketones such as perfluoroacetone; and fluorinated (e.g. perfluorinated) ethers such as perfluorodiethyl ether. Representative perfluorocarbons, which may for example contain up to 7 carbon atoms, include perfluoroalkanes such as perfluoromethane, perfluoroethane, perfluoropropanes, perfluorobutanes (e.g. perfluoro-n-butane, optionally in admixture with other isomers such as perfluoro-iso-butane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; perfluorocycloalkanes such as perfluorocyclobutane, perfluoromethylcyclobutane, perfluorodimethylcyclobutanes, perfluorotrimethyl-cyclobutanes, perfluorocyclopentane, perfluoromethyl-cyclopentane, perfluorodimethylcyclopentanes, perfluorocyclohexane, perfluoromethylcyclohexane and perfluorocycloheptane; and mixtures of any of the foregoing, including mixtures with more membrane-permeable gases such as air, nitrogen, carbon dioxide, oxygen etc., for example mixtures containing up to 90% of such more membrane-permeable gases.

The use of contrast agents comprising microbubbles of a perfluoroalkane such as perfluorobutane encapsulated by one or more phosphatidylserines is a particularly preferred embodiment of this aspect of the present invention.

Alternatively one may select membrane-forming lipid or other opsonisable amphiphilic materials which exhibit relatively low permeability to gases such as air, nitrogen, carbon dioxide, oxygen etc. Thus, for example, fluorinated membrane-forming lipid materials, e.g. wherein the fatty acyl groups are fluorinated, preferably perfluorinated, may be used to encapsulate a wide range of biocompatible gases (which term includes substances, including mixtures, substantially or completely in gaseous/vapour form at the normal human body temperature of 37° C.) in contrast agents useful in accordance with the invention. Examples of such gases include air, nitrogen, oxygen, carbon dioxide, hydrogen, nitrous oxide, inert gases (e.g. helium, argon, xenon or krypton), optionally halogenated silanes (e.g. tetramethylsilane), optionally halogenated low molecular weight hydrocarbons (e.g. containing up to 7 carbon atoms, for example alkanes such as methane, ethane, propanes, butanes or pentanes; cycloalkanes such as cyclobutane or cyclopentane; alkenes such as propene or butenes; alkynes such as acetylene; ethers; ketones; esters and halogenated versions of any of the foregoing, including perfluorocarbons such as those listed above), sulphur halides (e.g. sulphur hexafluoride or disulphur decafluoride) and mixtures of any of the foregoing.

It will be appreciated that the lipid or like membranes need not necessarily remain impermeable and/or stabilising to the gas microbubbles following arrest and/or uptake of the contrast agent by the liver, e.g. through arrest at surfaces (for example by specific interaction with receptors) or after being taken up by cells in accordance with known internalisation processes. Thus echogenicity following such arrest/uptake may derive from gas microbubbles stabilised by the original membrane-forming lipid or other opsonisable material, microbubbles where at least a part of the amphiphilic material is replaced by endogenous phospholipids, free gas microbubbles released from the contrast agent (if not dissolved or otherwise disposed of by the liver), or combinations of any of the foregoing. It will further be appreciated that stabilisation of the gas microbubbles may be enhanced if the gas has lower water solubility than normal blood gases such as oxygen, carbon dioxide and nitrogen.

The microbubbles of contrast agents used in accordance with the invention may conveniently have an average size of 0.1-10 μm, e.g. 1-7 μm, thereby permitting their free passage through the pulmonary system and eventual take up by organs such as the liver and spleen following intravenous administration. Such microbubbles are nonetheless of sufficient size to exhibit substantial echogenicity (a size-dependent property). The use of microbubbles of this size to enhance liver imaging may be contrasted with suggestions in prior art such as WO-A-9109629 that sizes of about 30-100 nm are desirable in order to ensure passage through the capillary fenestrations into the liver; gas microbubbles in this size range will exhibit significantly lower echogenicity than microbubbles within the preferred size ranges noted above.

If desired, a substance capable of stimulating blood flow in the liver, for example glucagon, and/or a substance capable of increasing hepatic uptake by stimulating phagocytosis, for example an antibody, antibody fragment or fibronectin, may be administered before, during or after administration of the contrast agent.

Preferred phospholipid-containing contrast agents useful in accordance with the invention may, for example, be administered in doses such that the amount of phospholipid injected is in the range 0.1-10 μg/kg bodyweight, e.g. 1-5 μg/kg. It will be appreciated that the use of such low levels of phospholipid is of substantial advantage in minimising possible toxic side effects.

Because of the rapid uptake in the liver, e.g. by the Kupffer cells, of preferred contrast agents useful in accordance with the invention, liver imaging of a patient may be performed as soon as 5-10 minutes after administration of the contrast agent, although it may be preferred to delay the investigation somewhat, e.g. until about 30 minutes after administration, to allow maximum uptake of contrast agent. The prolonged residence time of echogenic contrast agent in the liver permits effective imaging to be performed several hours (e.g. 2-8 hours) after administration.

Ultrasound imaging of the liver may, for example, be carried out using imaging frequencies of about 0.1-15 MHz, e.g. 1-10 MHz.

Representative imaging techniques which may be used in accordance with the invention include M-mode imaging, B-mode imaging, continuous wave Doppler imaging, pulsed wave Doppler techniques such as colour or power Doppler imaging, harmonic imaging, and combinations of any of the foregoing. The flexible nature of amphiphile-stabilised microbubble contrast agents used in accordance with the invention renders them particularly suitable for harmonic imaging techniques based on nonlinear effects such as higher harmonics (e.g. at 2, 3, 4 . . . times the imaging frequency), subharmonics (e.g. at ½, ⅓, ⅔, ¾ . . . times the imaging frequency) and ultraharmonics (e.g. at 3/2, 5/4 . . . times the imaging frequency), for example as described in U.S. Pat. No. 5,410,516; the use of second harmonic imaging may be particularly advantageous.

Harmonic imaging typically requires exposure of microbubble contrast agents to high intensity ultrasound irradiation in order to effect efficient conversion into harmonic ultrasound energy. Because the spatial distribution of ultrasound intensity in large tissue regions such as the liver tends to be very inhomogeneous as a result of inhomogeneities across the incident ultrasound beam and acoustic attenuation by the tissue, it may be necessary to employ very high incident intensities to obtain sufficient return signal intensities from distal parts of the imaged tissue; this may lead to rapid loss of contrast effect in tissue regions adjacent to the transducer, where the high intensity ultrasound irradiation may promote dissolution of microbubble gas into surrounding tissue fluids, and consequent loss of contrast effect, within as little as one second from the onset of irradiation. This inevitably limits the usefulness of such techniques in securing a full overview of a tissue region.

The flexible nature of contrast agents used in accordance with the present invention, however, causes them to exhibit high efficacy in harmonic energy conversion even at low incident ultrasound intensities, rendering them useful in harmonic imaging of deeply located regions of the liver at low ultrasound intensities which do not induce microbubble destruction phenomena in regions of the liver closer to the transducer. More generally, the flexible nature of the contrast agents permits their use in a variety of imaging modalities at low ultrasound intensity levels which do not destroy the contrast agent, thereby facilitating multiple scans of regions of interest within the liver, e.g. for confirmation purposes or using different imaging modalities.

If desired, however, higher ultrasound intensity levels may be used, and contrast may be detected by methods which detect microbubble destruction. Examples of such methods include phase sensitive techniques such as colour Doppler (e.g. as described in U.S. Pat. No. 5,425,366) or power Doppler, and phase insensitive techniques, e.g. as described in U.S. Pat. No. 5,456,257. Unlike the typically polymer-encapsulated microbubbles employed as contrast agents in accordance with U.S. Pat. No. 5,425,366, the present contrast agents may readily be designed to be extremely sensitive to incident ultrasound energy, for example by employing the stabilising amphiphilic material in the form of monolayers. Microbubble destruction may thereby be induced by surprisingly low levels of applied ultrasound energy, permitting efficient pseudo-Doppler imaging of the liver or parts thereof at very low incident ultrasound energy levels.

Detection techniques which may therefore be employed include non-Doppler correlation-based techniques such as colour velocity imaging and other techniques based on low correlation between successive ultrasound pulses processed in time or frequency domain, for example using RF signals optionally mixed with other signals, amplitude-demodulated RF signals, or RF signals processed using other techniques. Detection of real or apparent microbubble destruction may also be effected using nonlinear techniques, for example which analyse signals outside the bandwidth of the fundamental frequency of the emitted ultrasound pulse, such as higher harmonics, subharmonics or ultraharmonics or sum or difference frequencies, e.g. derived from the emitted pulse and such harmonics.

It has surprisingly been found that imaging techniques which are normally thought to involve microbubble destruction may be repeatedly performed using contrast agents in accordance with the present invention. Thus it would appear that such techniques may reversibly change the acoustic properties of the presently used contrast agents rather than destroying the microbubbles, thereby permitting repeated scanning to be performed.

It has also surprisingly been found that, even after prolonged residence time in the liver, contrast agents useful in accordance with the invention may produce Doppler signals with significantly broader spectra than those arising from blood and tissue motion. This may permit detection independent of disturbing motion artefacts by using higher filter settings than those normally employed in Doppler imaging. Higher gain settings may likewise be used, thereby permitting production of images with homogeneous contrast detection over the whole scan.

Contrast agents useful in accordance with the invention may be prepared by any appropriate method, advantageously by a process comprising the steps:

i) generating a dispersion of gas microbubbles in an aqueous medium containing an opsonisable amphiphilic material, such as a membrane-forming lipid;

ii) lyophilising the thus-obtained amphiphile-stabilised gas dispersion to yield a dried product; and iii) reconstituting the said dried product in an injectable carrier liquid.

Step (i) may, for example, be effected by subjecting the amphiphile-containing aqueous medium to any appropriate emulsion-generating technique, for example sonication, shaking, high pressure homogenisation, high speed stirring or high shear mixing, e.g. using a rotor-stator homogeniser, in the presence of the selected gas.

The aqueous medium may, if desired, contain additives which serve as viscosity enhancers and/or as solubility aids for the amphiphile, such as alcohols or polyols, e.g. glycerol and/or propylene glycol.

The gas employed in the emulsification step need not be that desired in the final product. Thus most of this gas content may be removed during the subsequent lyophilisation step and residual gas may be removed by evacuation of the dried product, to which an atmosphere or overpressure of the desired end product gas may then be applied. The emulsification gas may therefore be selected purely to optimise the emulsification process parameters, without regard to end product considerations.

Emulsification in the presence of a sulphur fluoride such as sulphur hexafluoride or a fluorinated low molecular weight hydrocarbon gas such as a perfluoroalkane or perfluorocycloalkane, preferably containing 4 or 5 carbon atoms, may be particularly advantageous in terms of ultimately yielding end products with consistent and narrowly distributed microbubble sizes.

The emulsification is conveniently effected at about ambient temperature, e.g. at ca. 25±10° C. It may be necessary initially to heat the aqueous medium to facilitate hydration and thus dispersion of the amphiphile and then allow it to equilibrate to ambient temperature prior to emulsification.

Dispersions produced according to step (i) may advantageously be subjected to one or more washing steps prior to lyophilisation step (ii), in order to separate and remove additives such as viscosity enhancers and solubility aids, as well as unwanted material such as non-gas-containing colloidal particles and undersized and/or oversized microbubbles. Such washing may be effected in per se known manner, the microbubbles being separated using techniques such as flotation or centrifugation. In this way size-fractionated microbubble dispersions may be prepared wherein at least 90% of the microbubbles have sizes within a 2 µm range, e.g. having a volume mean diameter within the range 2-5 µm.

It may be advantageous to conduct step (ii) in the presence of one or more cryoprotective and/or lyoprotective and/or bulking agents, such agent(s) advantageously being added after the washing steps, prior to lyophilisation. A substantial list of agents with cryoprotective and/or lyoprotective effects is given in Acta Pharm. Technol. 34(3), pp. 129-139 (1988), the contents of which are incorporated herein by reference. Examples of such agents include alcohols (e.g. aliphatic alcohols such as t-butanol), polyols such as glycerol, aminoacids such as glycine, carbohydrates (e.g. sugars such as sucrose, mannitol, trehalose, glucose, lactose and cyclodextrins, or polysaccharides such as dextran) and polyglycols such as polyethylene glycol, the use of physiologically well-tolerated sugars such as sucrose (e.g. in an amount such as to render the product isotonic or somewhat hypertonic) being preferred.

Lyophilisation of the gas dispersion may, for example, be effected by initially freezing it and thereafter lyophilising the frozen gas dispersion, for example in per se generally known manner. Such frozen gas dispersions may be stored frozen and thawed when desired, e.g. by simple warming and/or by addition of a carrier liquid, to regenerate microbubble dispersions useful as contrast agents in accordance with the invention.

Since the dried product will normally be reconstituted in accordance with step (iii) above prior to administration, the gas dispersion may advantageously be filled into sealable vials prior to lyophilisation so as to give vials each containing an appropriate amount, e.g. a single dosage unit, of lyophilised dried product for reconstitution into an injectable form. By lyophilising the gas dispersion in individual vials rather than in bulk, handling of the delicate honeycomb-like structure of the lyophilised product and the risk of at least partially degrading this structure are avoided. Following lyophilisation and any optional further evacuation of gas and introduction into the headspace of gas desired to be present as microbubbles in the ultimately formulated contrast agent, the vials may be sealed with an appropriate closure.

In general the frozen gas dispersion or the dried product from step (ii), e.g. after any necessary and/or desired supplementation or exchange of gas content, may be reconstituted by addition of an appropriate injectable carrier liquid such as sterile pyrogen-free water or saline for injection. Where the dried product is contained in a vial this is conveniently sealed with a septum through which the carrier liquid may be injected using a syringe. It may be advantageous to mix or gently shake the product following reconstitution; no more than gentle hand-shaking may be required to give reproducible products with consistent microbubble size.

Another method of preparing contrast agents useful in accordance with the invention comprises contacting powdered opsonisable amphiphilic material with gas, admixing the powdered amphiphile with aqueous carrier liquid to form a suspension of gas-filled microbubbles, allowing the microbubbles to form a layer, separating this layer and washing the separated microbubbles (e.g. as described in U.S. Pat. No. 5,445,813. A further method which may be used involves shaking an aqueous solution comprising opsonisable amphiphilic material in the presence of gas (e.g. as described in WO-A-9428780).

The following non-limitative Examples serve to illustrate the invention.

A—PREPARATION OF CONTRAST AGENTS

Example 1 a) Preparation of Perfluorobutane Microbubble Dispersions by Shaking 25.3 mg hydrogenated egg phosphatidylserine is added to 12.5 ml water containing 5.4% (w/w) of a mixture of propylene glycol and glycerol (3:10 w/w). The phospholipid material is hydrated by heating to 70° C. for approximately 30 minutes, followed by cooling to room temperature. 11 ml of the dispersion is divided in 1 ml portions between eleven 2 ml vials, and the head space of the vials is filled with perfluoro-n-butane gas. The vials are securely capped and shaken for 45 seconds using an Espe CapMix7 (mixer for dental materials). The resulting microbubble dispersions are combined in four larger vials and centrifuged at 2000 rpm for 5 minutes, giving a turbid infranatant below a floating layer of microbubbles. The infranatant is removed by a syringe and replaced with an equal volume of water at neutral pH. The washing step is repeated, but now the infranatant is replaced by 10% (w/w) sucrose. 2 ml portions of the resulting dispersion are divided between 10 ml flat-bottomed vials specially designed for lyophilisation, and the vials are cooled to −47° C. and lyophilised for approximately 48 hours, giving a white fluffy solid substance. The vials are transferred to a vacuum chamber, and air is removed by a vacuum pump and replaced by perfluoro-n-butane gas. Prior to use, water is added and the vials are gently hand-shaken for several seconds, giving microbubble dispersions suitable as ultrasound contrast agents.

b) Preparation of Perfluorobutane Microbubble Dispersions by Rotor Stator Mixing 500.4 mg hydrogenated egg phosphatidylserine is added to 100 ml water containing 5.4% (w/w) of a mixture of propylene glycol and glycerol (3:10 w/w). The mixture is shaken and heated to 80° C. for five minutes, allowed to cool to room temperature, shaken again and left standing overnight prior to use.

50 ml of the resulting solution is transferred to a round-bottomed flask with a conical neck. The flask is fitted with a glass jacket having a temperature control inlet and outlet connected to a water bath maintained at 25° C. A rotor stator mixing shaft is introduced into the solution and to avoid gas leakage the space between the neck wall and the mixing shaft is sealed with a specially designed metal plug fitted with a gas inlet/outlet connection for adjustment of gas content and pressure control. The gas outlet is connected to a vacuum pump and the solution is degassed for one minute. An atmosphere of perfluoro-n-butane gas is then applied through the gas inlet.

The solution is homogenised at 23000 rpm for 10 minutes, keeping the rotor stator mixing shaft such that the openings are slightly above the surface of the liquid. A white coloured creamy dispersion is obtained, which is transferred to a sealable container and flushed with perfluoro-n-butane. The dispersion is then transferred to a separating funnel and centrifuged at 12000 rpm for 30 minutes, yielding a creamy layer of bubbles at the top and a turbid infranatant. The infranatant is removed and replaced with water. The centrifugation is then repeated twice, but now at 12000 rpm for 15 minutes. After the last centrifugation, the supernatant is replaced by 10% (w/w) sucrose. 2 ml portions of the resulting dispersion are divided between 10 ml flat-bottomed vials specially designed for lyophilisation, and the vials are cooled to −47° C. and lyophilised for approximately 48 hours, giving a white fluffy solid substance. The vials are now transferred to a vacuum chamber, and air is removed by a vacuum pump and replaced by perfluoro-n-butane gas. Prior to use, water is added and the vials are gently hand-shaken for several seconds, giving microbubble dispersions suitable as ultrasound contrast agents.

c) Preparation of Perfluorobutane Microbubble Dispersions by Sonication 500.4 mg hydrogenated egg phosphatidylserine is added to 100 ml water containing 5.4% (w/w) of a mixture of propylene glycol and glycerol (3:10 w/w). The mixture is shaken and heated to 80° C. for five minutes, allowed to cool to room temperature, shaken again and left standing overnight prior to use.

This solution is pumped through a 4 ml sonicator flow-through cell and exposed to ultrasound at 20 kHz with an amplitude of 90 µm. The diameter of the sonicator horn is 1.3 cm, the inner diameter of the cell is 2.1 cm and the distance between the horn and the bottom of the cell is 1 cm. The lipid solution is mixed with perfluoro-n-butane at a ratio of 1:2 v/v before it enters the sonicator cell (20 ml/min lipid solution and 40 ml/min perfluoro-n-butane gas). The temperature is kept at 33° C. A white and creamy dispersion is obtained which is filled into a container and flushed with perfluoro-n-butane.

Characterisation

The size distribution and volume concentration of the microbubbles are measured using a Coulter Counter Mark II apparatus fitted with a 50 µm aperture with a measuring range of 1-30 µm. 20 µl samples are diluted in 200 ml saline saturated with air at room temperature, and allowed to equilibrate for 3 minutes prior to measurement.

Ultrasound characterisation is performed on a experimental set up slightly modified from de Jong, N. and Hoff, L. as described in "Ultrasound scattering properties of Albunex microspheres", Ultrasonics 31(3), pp. 175-181 (1993). This instrumentation measures the ultrasound attenuation efficacy in the frequency range 2-8 MHz of a dilute suspension of contrast agent. During the attenuation measurement a pressure stability test is performed by exposing the sample to an overpressure of 120 mmHg for 90 seconds. Typically 2-3 µl of sample is diluted in 55 ml Isoton II and the diluted sample suspension is stirred for 3 minutes prior to analysis. As primary response parameter the attenuation at 3.5 MHz is used, together with the recovery attenuation value at 3.5 MHz after release of the overpressure.

TABLE 1.1

In vitro characteristics of bubble dispersions produced according to Example 1(a)-(c). Number and volume weighted concentrations and volume mean diameters. Acoustic properties measured according to description above.

| Production method (Example No.) | Number conc. [$10^6$/ml] | Vol. conc. [%] | Vol. mean diam. [μm] | Atten. at 3.5 Mhz [dB/cm] | Survival after over-pressure [%] | Freq. at max. atten. [MHz] |
|---|---|---|---|---|---|---|
| 1(a) | 1519 | 1.45 | 3.91 | 30.46 | 100 | 4.1 |
| 1(b) | 10518 | 6.51 | 3.16 | 150.4 | 96 | 4.3 |
| 1(c) | 23389 | 9.57 | 3.83 | 117 | 100 | 3.5 |

Example 2

Preparation of Various Microbubble Dispersions By Rotor Stator Mixing, Lyophilisation and Gas Exchange The gas contents of five samples prepared according to Example 1(b) above are replaced with air, perfluorobutane, sulphur hexafluoride, trifluoromethylsulphur pentafluoride and tetramethylsilane respectively, according to the following procedure:

Two samples containing lyophilised product from Example 1(b) are placed in a desiccator having a gas inlet and a gas outlet. The desiccator is connected to a Buchi 168 vacuum/distiller controller which permits controlled evacuation of the samples and inlet of a selected gas. The samples are evacuated at approximately 10 mbar for 5 minutes, whereafter the pressure is increased to atmospheric by inlet of the selected gas, followed by careful capping of the vials. The procedure is repeated using further pairs of samples for each of the selected gases.

2 ml distilled water is added to each vial and the vials are gently hand-shaken prior to use. The resulting microbubble dispersions are characterised with respect to size distribution measurements as described in Example 1.

The results are summarised in Table 2.1.

TABLE 2.1

In vitro characteristics of phosphatidylserine-stabilised microbubble dispersions produced according to Example 2 - number and volume weighted concentrations and volume mean diameters.

| Gas | Number conc. [$10^6$/ml] | Number mean diam. [μm] | Vol. conc. [%] | Vol. mean diam. [μm] |
|---|---|---|---|---|
| Perfluorobutane | 9756 | 1.8 | 4.9 | 5.8 |
| Trifluoromethyl-Sulphur pentafluoride | 10243 | 1.9 | 5.9 | 3.5 |
| Sulphur hexafluoride | 9927 | 1.9 | 5.7 | 3.2 |
| Tetramethylsilane | 9947 | 1.9 | 6.1 | 3.7 |
| Air | 9909 | 1.9 | 6.4 | 4.0 |

As will be seen from the above results there is no significant change in size distribution upon gas exchange, demonstrating that the preformed microbubble size is substantially preserved during both lyophilisation and reconstitution.

Method of Ultrasound Liver Imaging

Example 3

Liver Imaging in Rabbits

Contrast agents prepared in accordance with Example 1 were intravenously injected at a dosage of 5 μg phospholipid/kg into rabbits sedated with 0.65 mg/kg of a mixture of xylazine hydrochloride and ketamine hydrochloride administered intramuscularly. An ultrasound transducer was placed on shaved skin above the liver region. Transabdominal studies performed using B-mode imaging (5-7 MHz), colour Doppler imaging, second harmonic imaging, power Doppler imaging, combinations of harmonic and colour Doppler imaging and combinations of harmonic and power Doppler imaging indicated the presence of implanted VX2 tumours in the liver and correlated with results obtained by X-ray radiography using arterially administered ethiodol as contrast agent.

Example 4

Liver Imaging in Woodchucks

The procedures of Example 3 were used to detect the presence of naturally occurring liver tumours in woodchucks. The results correlated with histological examination of the livers.

Example 5

Liver Imaging in Dogs

66 μl of a 1% microbubble dispersion prepared as in Example 1(a) was injected intravenously into a 20 kg mongrel dog. Second harmonic images of the liver were made before and 10 minutes after injection using an ATL HDI-3000 scanner equipped for second harmonic imaging, with an emission frequency of 2.5 MHz, and a P5-3 phased array sector scan transducer. The power output of the scanner was set to a low level, with a mechanical index (MI) of 0.3. The transducer was positioned in a subcostal location close to the midline. Contrast induced enhancement of the liver in the images obtained after injection was stable and appeared not to be reduced with time despite continuous ultrasound scanning. When compared with the baseline image acquired before injection, evident contrast enhancement of the whole liver to a depth of more than 10 cm could be seen.

Example 6

Imaging of Tumour in a Human Liver

10 μl of a 1% microbubble dispersion prepared as in Example 1(a) was injected intravenously into a female human patient. Fundamental B-mode imaging of the liver performed with an ATL HD1-3000 scanner clearly demonstrated vascular enhancement of vessels around metastatic lesions. 15 minutes after injection, lesions which were isoechoic with surrounding tissue in the baseline scan, and were thus initially difficult to see, exhibited enhanced visibility as the surrounding normal liver tissue became more echogenic. The effect was even more pronounced 30 minutes after injection, demonstrating lasting and improved contrast effects after prolonged residence time of the contrast agent in the liver.

Example 7

Cellular Distribution of Contrast Agent After In Vivo Uptake in Rat Liver

Three unanaesthetised rats were each given single intravenous injections of a 1% microbubble dispersion prepared as in Example 1(a) (50 μl microbubbles per kg body weight, corresponding to several hundred times a typical imaging dose in humans) into the tail vein. Control rats were similarly injected with saline. Following injection the rats were anaesthetised. Ten minutes after injection the abdomen and chest wall were incised, and the liver was perfused with buffer (100 mM HEPES, pH 7.4) until it was pale and then with the same buffer containing glutaraldehyde (2% v/v) until it was hard. The liver was then excised and cut into thin slices. Tissue samples were processed into epoxy resin, and semi-thin (ca. 1 μm) sections were cut for examination by light microscopy. Appropriate areas were selected on the basis of light microscopy and small area ultra-thin sections were cut therefrom and stained with osmium tetroxide for electron microscopy.

Figure 1A:
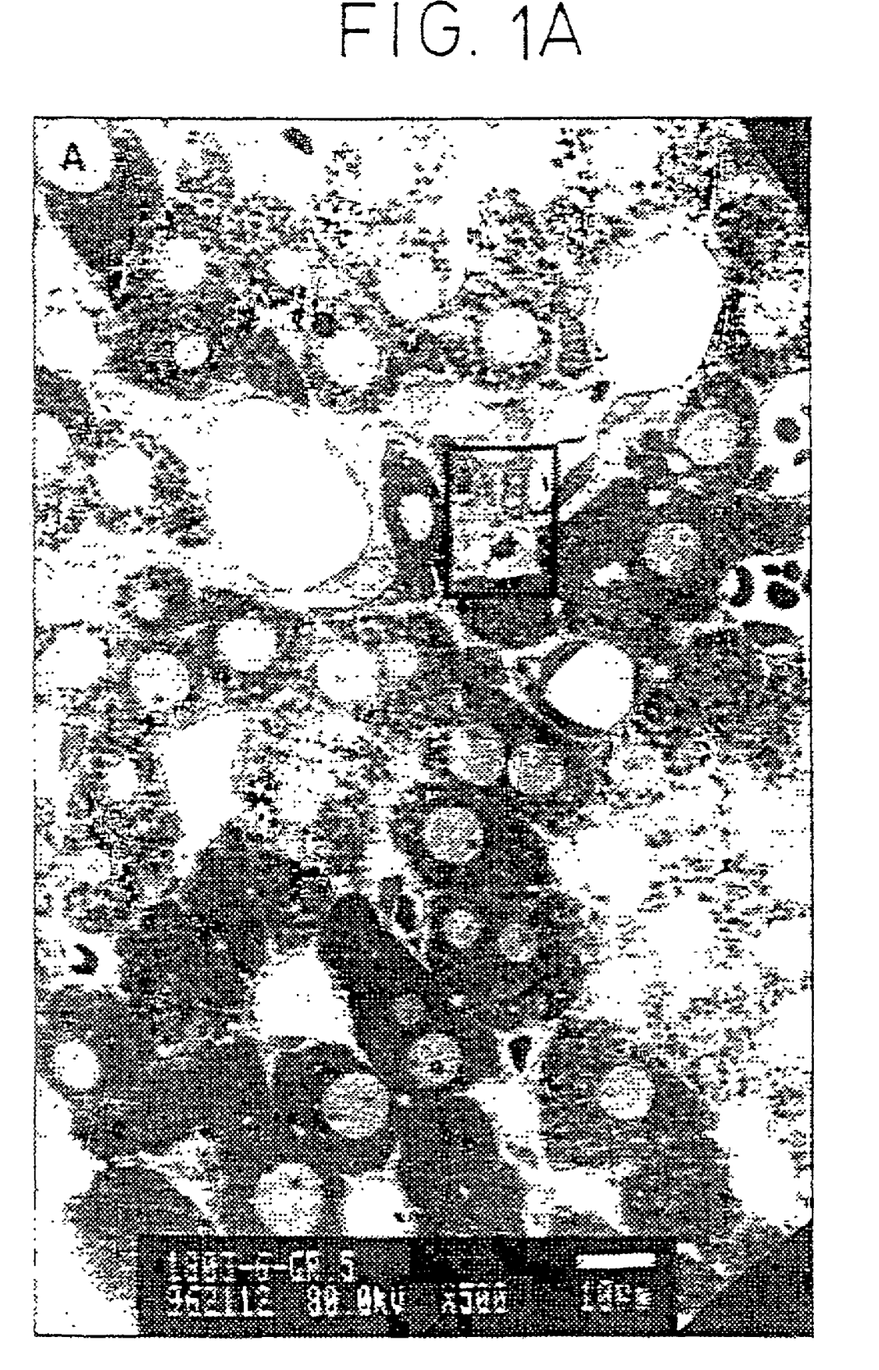
FIG. 1A is an electron micrograph of a sample from the liver of a saline-treated control rat, obtained as described in Example 7.
Figure 1B:
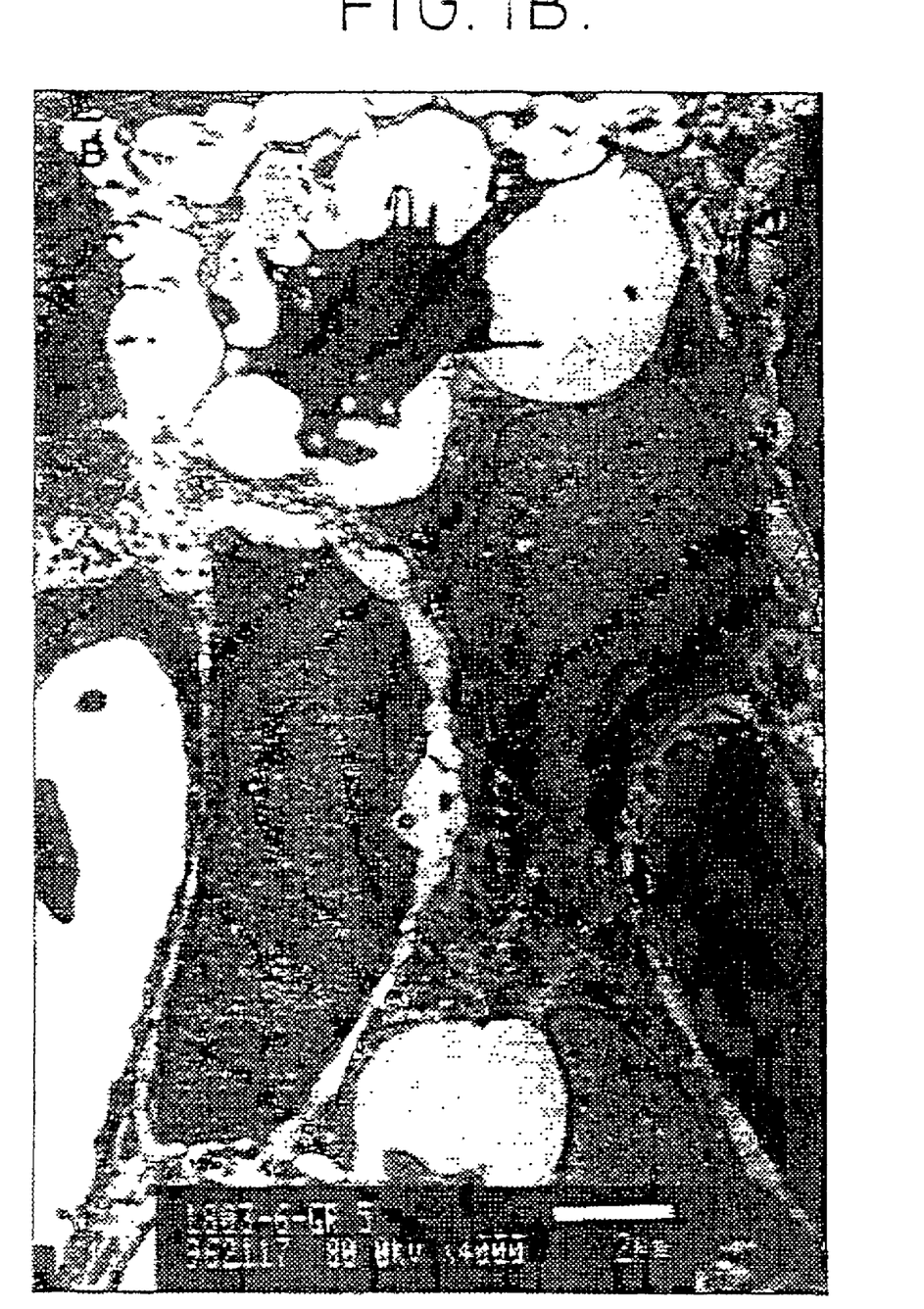
FIG. 1B is an enlargement of the marked part of FIG. 1A.
Figure 1C:
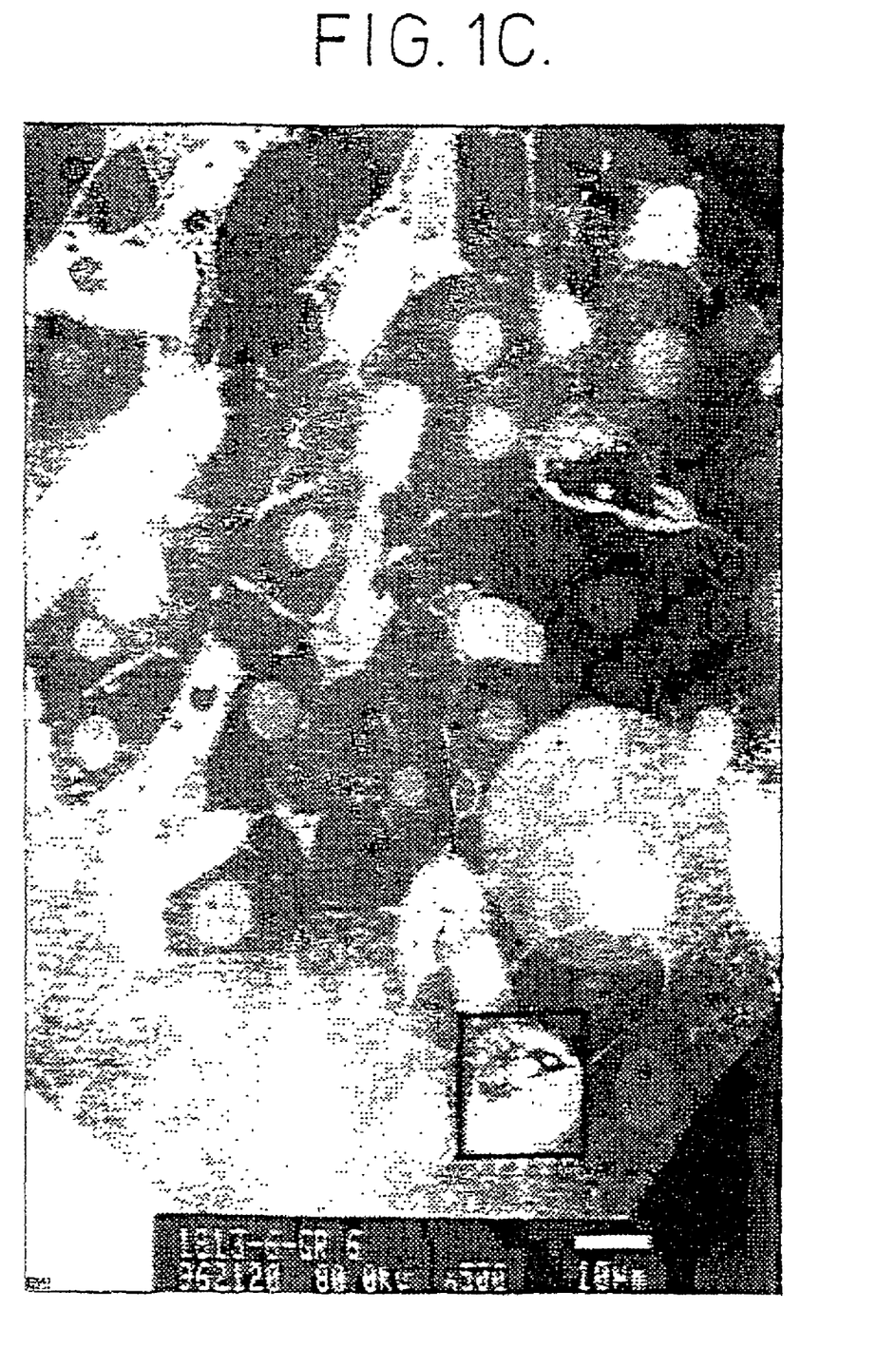
FIG. 1C is an electron micrograph of a sample from the liver of a contrast agent-treated rat, obtained as described in Example 7.
Figure 1D:
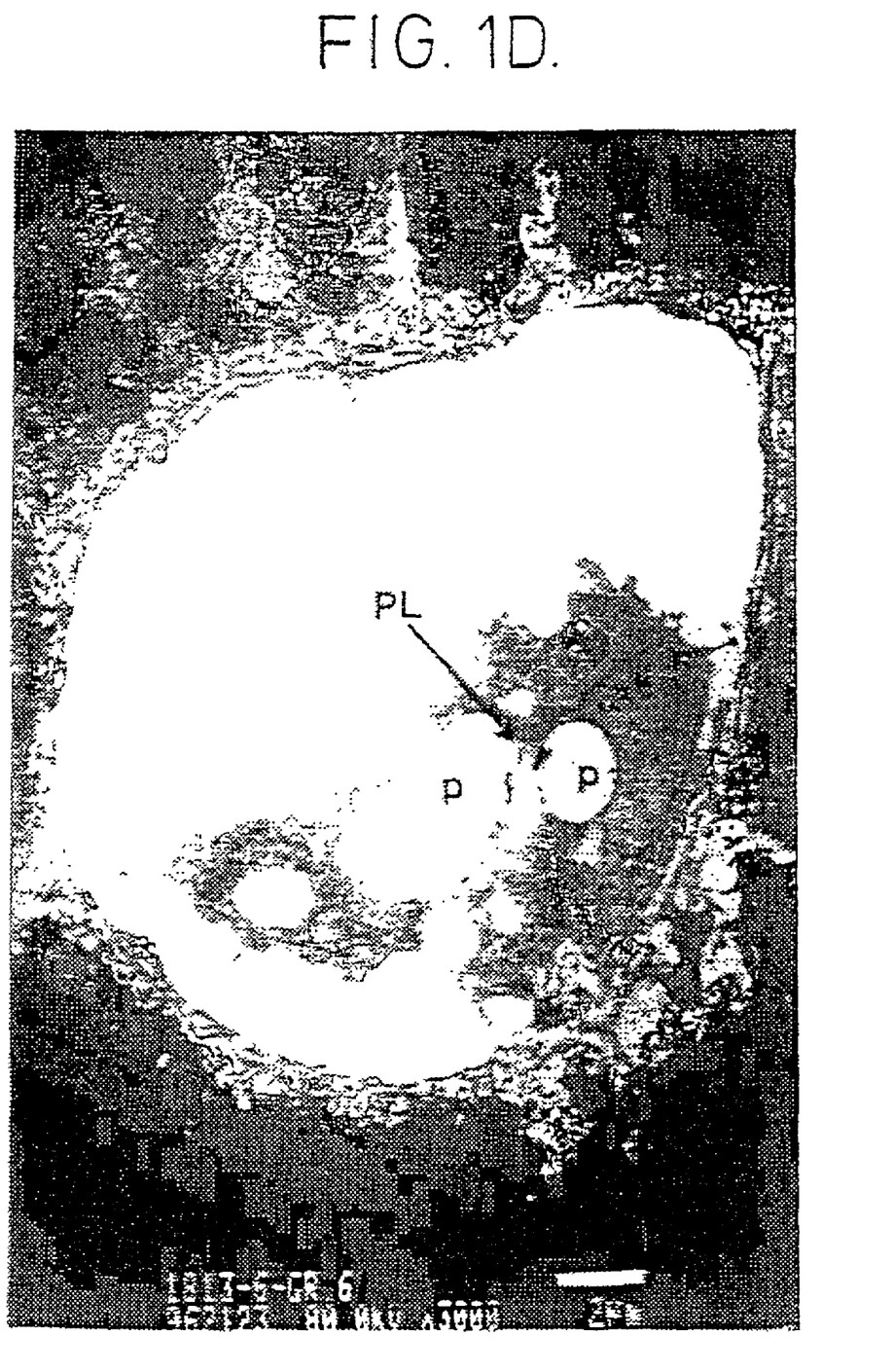
FIG. 1D is an enlargement of the marked part of FIG. 1C.

Control electron micrographs in respect of samples from saline-treated rats (see FIG. 1A and the enlargement therefrom in FIG. 1B) revealed no vacuolisation in Kupffer cells, endothelial cells or parenchymal cells. Electron micrographs in respect of samples from contrast agent-treated rats (see FIG. 1C and the enlargement therefrom in FIG. 1D) revealed that some Kupffer cells had internalised microparticles or microbubbles ("p") No such microparticles or microbubbles were evident in parenchymal or endothelial cells. Furthermore, densely stained material, believed to be phospholipid material ("PL"), could be observed at the borders of some of the microparticles or microbubbles.

What is claimed is:

1. A method of ultrasound imaging which comprises administering to a human or non-human animal subject a contrast-enhancing amount of a contrast agent comprising microbubbles of biocompatible gas stabilised by encapsulating membranes comprising monolayers of opsonisable phospholipid material including at least 50% of negatively charged phospholipid, wherein said negatively charged phospholipid comprises at least one phosphatidylserine, whereby at least a proportion of said membrane-encapsulated microbubbles are taken up in the liver of the subject and exhibit a contrast-generating residence time of 2-8 hours following such administration, and generating an ultrasound image of said uptaken contrast agent microbubbles in at least a part of the liver.

2. A method as claimed in claim 1 wherein said biocompatible gas is sulphur hexafluoride, disulphur decafluoride, a perfluoroacetone, a perfluorodiethyl ether, or a perfluorocarbon.

3. A method as claimed in claim 2 wherein said perfluorocarbon is a perfluorobutane.

4. A method as claimed in claim 1 wherein said biocompatible gas is selected from air, nitrogen, carbon dioxide, oxygen, hydrogen, nitrous oxide, an inert gas, an optionally halogenated low molecular weight hydrocarbon, a sulphur halide and mixtures of any of the foregoing.

5. A method as claimed in claim 1 wherein a substance capable of stimulating blood flow in the liver and/or a substance capable of increasing hepatic uptake by stimulating phagocytosis is administered before, during or after administration of said contrast agent.

6. A method as claimed in claim 1 wherein the ultrasound image is generated by second harmonic imaging.

7. A method as claimed in claim 1 wherein the ultrasound image is generated using techniques based on non-linear effects.

8. A method as claimed in claim 1 wherein generation of the ultrasound image is commenced 5-30 minutes after administration of the contrast agent.

9. A method as claimed in claim 1 wherein generation of the ultrasound imaging is effected using B-mode or Doppler imaging.

10. A method as claimed in claim 1 wherein generation of the ultrasound image is effected at low ultrasound intensity levels using multiple scans.

* * * * *